(12) United States Patent
Wenz et al.

(10) Patent No.: US 6,420,454 B1
(45) Date of Patent: Jul. 16, 2002

(54) BONE SEALANTS

(75) Inventors: Robert Wenz, Wöllstadt; Ralf Krotz, Wiesloch; Wolfgang Ritter, Offstein, all of (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/453,492

(22) Filed: Dec. 3, 1999

(30) Foreign Application Priority Data

Dec. 19, 1998 (DE) .......................................... 198 58 891

(51) Int. Cl.[7] .......................... A61L 24/06; C08U 67/04; C08U 5/06

(52) U.S. Cl. ........................ 523/118; 523/105; 523/113; 524/377; 524/378; 427/2.26; 427/2.3

(58) Field of Search ................................ 523/105, 113, 523/115, 116, 118; 524/377, 378; 427/2.26, 2.3

(56) References Cited

U.S. PATENT DOCUMENTS 5,783,205 A * 7/1998 Berggren et al. ........... 523/125

* cited by examiner

*Primary Examiner*—Peter Szekely
(74) *Attorney, Agent, or Firm*—Millen, White, Zelano & Branigan, P.C.

(57) ABSTRACT

The present invention relates to improved bone sealants for staunching local haemorrhages on bones, which are characterized in that the bone sealant consists of a polyester oligomer synthesized from polyol, lactide and glycolide, and water-soulble polymers.

21 Claims, No Drawings

BONE SEALANTS

The present invention relates to improved bone sealants for staunching local hemorrhages on the bone and as a carrier material for active compounds.

Bone sealants or bone waxes are used for the mechanical closure of hemmorrhaging bone wounds. Absorbable bone sealants have the advantage compared with non-absorbable bone waxes that they are completely metabolized by the body, without inflammatory symptoms, in particular macrophage-induced foreign-body reactions.

Absorbable waxes of this type for mechanical hemostasis on endogenous hard tissue, in particular bone, are known and, for example, are the subject of EP 0 100 981. The waxes or sealants described there are distinguished in that they consist of waxy polyester oligomers of lower hydroxycarboxylic acids, which are highly viscous to solid at body temperature. On account of their structure, these waxes are degradable by endogenous metabolic mechanisms, the rate of degradation being adjustable in a manner known per se. Oligomers of glycolic acid are degraded more rapidly by the endogenous metabolism than those of lactic acid. The degradation rate is thus regulatable, for example, by mixed esterification of the two known hydroxycarboxylic acids. The preferred waxes have average molecular weights in the range from about 200 to 1500 and in particular in the range from about 300 to 1000.

The regulate the average molecular weight of these polyester oligomers, the patent mentioned proposes additionally using monofunctional and/or difunctional alcohols or carboxylic acids or carboxylic anhydrides and/or primary or secondary monoamines. In a manner known per se, it is then possible by choice of suitable mixing ratios of hydrooxycarboxylic acids and additional monofunctional or difunctional components to predetermine an average molecular weight which finally established itself.

German Patent 37 16 302 relates to a continuing optimization of absorbable waxes of this type. It is described in this patent that body- and tissue-compatible waxes are particularly obtained if—observing the general legalities of the previously mentioned patent—a very specific trifunctional alcohol, namely glycerol, is empolyed for adjustment of the average molecular weight. The combination of glycerol with oligoesters of lactic acid and/or of glycolic acid leads to degradable waxy components of the type mentioned, which are distinguished on implantation into living body tissue by a particularly highly pronounced physical tolerability.

Disadvantages, however, are furthermore also seen in the practical use of these known and highly tolerable substances, such as, for example, strong adhesion to plastics, poor extrudability or alternatively a non-optimum viscosity at room temperature.

The teaching of the present invention therefore starts from the object of furthermore improving body-absorbable bone sealants in a number of ways. In particular, bone sealant materials are to be made available which do not have the disadvantages of strong adhesion to plastics, such as, for example, surgical gloves, and furthermore have an improved extrudability from packaging materials together with improved mechanical properties, in particular the viscosity at room temperature and at body temperature, while maintaining the haemostatic properties.

The teaching of the invention for solving this many-sided objective starts from the knowledge that such a demanding bone sealant can only be obtained in a very specific formulation of the individual components.

Surprisingly, it has now been found that the blending of polyester oligomers of very specific compositions with water-soluble polymers leads to the bone sealant materials which are improved in many respects.

The invention accordingly relates to a bone sealant for staunching local hemorrhages on the bone, which comprises a polyester oligomer, synthesized from polyol, lactide, and glycolide and water-soluble polymers.

The oligomer segments of the optimized bone waxes described according to the invention are derived from lactic acid and glycolic acid. In general, the readily handleable dimerization products, i.e., the lactide and the glycolide, are employed, but it is also possible to take the monomeric hydroxycarboxylic acids as starting materials. Lactic acid or lactic acid dimers can be used as the optically active component or alternatively as a mixture of the optically active compounds as the D, L-lactide.

As the third component, i.e., as the coreactant, a polyol is added in a known manner for the adjustment of the desired degree of oligomerization. Glycerol is preferably employed as a polyfunctional alcohol.

In accordance with the invention, the described polyester oligomers are blended with water-soluble polymers.

Suitable water-soluble polymers are polyethylene glycol or copolyethers of ethylene glycol and propylene glycol. These preferably have a molecular weight of 1,000 to 10,000, especially 6,000 to 10,000. In particularly preferred embodiment of this invention, PEG 8000 is used. Either a water-soluble polymer or alternatively a mixture of a number of water-soluble polymers can be used.

Blending with the polyester oligomers is preferably carried out such that the content of water-soluble polymers is 5–50%. Particularly preferably, the content is 15–30%.

In particularly preferred embodiments of the present invention, the polyester oligomers are synthesized from 1 part of glycerol and X parts of lactide and Y parts of glycolide, where X and Y in each case independently of one another can be 1, 2 or 3.

In this case, in particular, those are particularly preferred in which X+Y is $\leq 4$.

The polyester oligomers are prepared by the customary condensation processes, which are known and descirbed in the patents cited above, and therefore do not have to be described in greater detail here. The polyester oligomers are thus also characterized by an average molecular weight in the range from 200 to 1500 and preferably in the range from 300 to 1000.

Particularly preferred embodiments are those in which the polyester oligomers are composed of 1 part of glycerol, 2 parts of lactide and 1 part of glycolide or alternatively of 1 part of glycerol and 2 parts of lactide and glycolide in each case.

In a very particularly preferred embodiment, the polyester oligomer consists of 1 part of glycerol, 1 part of lactide and 3 parts of glycolide.

Furthermore, it was surprisingly found that preferred products can also be prepared if, during the condensation reaction, a temperature of 140° C. to 160° C., preferably of 145° C. to 155° C., is chosen. These temperatures are lower in comparison with the temperatures otherwise customary in condensation reactions.

The oligomers can then either be sterilized—preferably γ-sterilization—or else alternatively directly further processed.

The blending of polyester oligomers of this type with 15–30% of water-soluble polymer leads to particularly preferred bone sealant materials according according to the invention.

The blending of the polyester oligomers with the water-soluble polymers can be carried out either by kneading by hand or—which is preferred and simpler to handle—by means of a kneader at somewhat elevated temperatures. Preferably, for complete degassing, vacuum is additionally applied.

The products are preferably stored in sterilized form, γ-sterilization preferably being carried out.

The bone sealants according to the invention are used for staunching local hemorrhages on the bone. They exhibit many improved properties with respect to their use.

The properties according to the invention are tested in the customary manner on anaesthetized pigs by direct application to the sternum after thoracotomy. Inter alia, the adhesion properties of the blend to the spongy bone of the sternum, the assessment of the stickiness on the surgical glove, the application properties, the assessment of the hemostasis after specific time intervals as well as the assessment of the penetration power into the spongiosa and assessment of the surface film are the test criteria.

The improved bone waxes now exhibit a low adhesion to plastics (e.g. surgical gloves), and they have an improved viscosity at room temperature and body temperature, an improved extrudability and they show outstanding hemostatic properties.

The leads to an outstanding practical handleability of these bone sealants, which significantly facilitates the work of the operator. The "stickiness" of the waxes is significantly reduced, and also the stringiness, which up to now had caused great difficulties in products containing lactic acid. Furthermore, good tissue compatibility is also guaranteed.

Using the bone sealants described in this invention, improved products are now available which have considerable importance.

It is also assumed that a person skilled in the art can utilize the above description to the widest possible extent without further details. The preferred embodiments, therefore, are only to be interpreted as descriptive, but in no way as in any manner limiting disclosure.

The complete disclosure of all applications and publications mentioned above and below, as well as German patent application 198 58 891.7, are incorporated herein by reference.

The following examples are intended to illustrate the invention in greater detail.

EXAMPLE A

General procedure for the preparation of the polyester oligomers

Glycerol, lactide and glycolide are weighed into the apparatus and the catalyst is added by pipette. The crystal magma is heated to 100° C. under nitrogen and with stirring in the course of 1 h, fused at 100° C. in the course of 15 min, then heated to 195° C. in, the course of 1 h and left at 193°–197° C. for 5 h. The oil bath is then removed and the product is dispensed hot.

In Example 1, a composition of glycerol:L-lactide: glycolide of 1:2:1 was chosen, and in Example 2 a composition of glycerol:D,L-lactide:glycolide of 1:1:3.

The batches are summarized in Table 1.

TABLE 1

| Ex. | Glycerol | Lactide | Glycolide | Cat.* | Final weight | Product |
|---|---|---|---|---|---|---|
| 1 | 1.6 M | L-; 3.2 M | 1.6 M | 2.24 ml | 787 g | clear, colorless |
| 2 | 1.3 M | D,L; 1.3 M | 3.9 M | 2.21 ml | 749 g | clear, colorless |

*Catalyst: $H_3PO_4$ 0.5% (based on amount of lactide and glycolide)

The samples were then dispensed into cryovials for γ-sterilization.

EXAMPLE B

Alternative general procedure for the preparation of the polyester oligomers

Glycerol, lactide (L-lactide or D,L-lactide) and glycolide are weighed into the apparatus and the catalyst is added by pipette. The crystal magma is heated to 100° C. under nitrogen and with stirring in the course of 1 h, fused at 100° C. in the course of 15 min, then heated to 150° C. in the course of 30 min and then allowed to react at 148°–152° C. for 5 h. The oil bath is then removed and the product is dispensed hot.

In example 3, a ratio of glycerol:D,L-lactide:glycolide of 1:1:3 was chosen, and in Example 4 a ratio of glycerol:D,L-lactide:glycolide of 1:2:2.

The batches are summarized in Table 2.

TABLE 2

| Ex. | Glycerol | Lactide | Glycolide | Cat.* | Product |
|---|---|---|---|---|---|
| 3 | 1.3 M | 1.3 M | 3.9 M | 2.21 ml | clear colorless |
| 4 | 1.3 M | 2.6 M | 2.6 M | 2.34 ml | clear, colorless |

*Catalyst: $H_3PO_4$ 0.5% (based on amount of lactide and glycolide)

The samples were then dispensed into cryovials for γ-sterilization.

EXAMPLE C

General procedure for blending polyester oligomers, prepared according to Examples A and B, with polyethylene glycol (PEG) in a kneader The kneader is first heated by means of a water bath, and the appropriate copolymer is also heated in the water bath at the same time (water bath 90° C.). The PEG is then added to the bone sealant in portions at a kneader temperature of about 70° C. and briefly kneaded in between. The PEG then melts after a short time, and afterwards a minimal vacuum is cautiously applied (foaming). The mixture is then kneaded for 1.5 h at about 80° C. The kneader is switched off and the mixture is allowed to stand for about another 30 min under full vacuum. The samples can then be dispensed and subjected to γ-sterilization.

EXAMPLE 5

The glycero-oligo-L-lactide-co-glycolide from Example 1 (ratio 1:2:1) is mixed with PEG 10,000 (Fluka, #81268) in the ratio 75% to 25% of PEG according to the general procedure and then sterilized. A bone sealant is obtained which can be readily applied.

EXAMPLE 6

The glycero-oligo-L-lactide-co-glycolide from Example 1 (1:2:1) is mixed with PEG 8000 (Fluka, #81268) in the ratio 60% to 40% of PEG according to procedure C and then sterilized. The finished bone sealant exhibits a very low stickiness on gloves, is soft and can be readily applied and exhibits good haemostasis.

EXAMPLE 7

The polyoligoester (D,L-lactide) from Example 2 (1:1:3) is mixed with PEG 8000 (Fluka, #81268) in the ratio 80% to 20% of PEG according to procedure C and then γ-sterilized.

EXAMPLE 8

The glycero-oligo-D,L-lactide-co-glycolide from Example 4 (1:2:2) is mixed with PEG 8000 (Fluka, #81268) in the ratio 70% to 30% of PEG according to the general mixing procedure. An outstandingly suitable bone sealant is obtained. This product is not sticky, can be very readily applied and the haemostasis is outstanding.

EXAMPLE 9

The glycero-oligo-D,L-lactide-co-glycolide from Example 3 (1:1:3) is mixed with PEG 8000 (Fluka, #81268) in the ratio 70% to 30% of PEG according to general procedure C and then γ-sterilized. This leads to an outstandingly suitable bone sealant, which is not sticky, has a good consistency, can be readily applied and forms an even film. Moreover, heomstatis with this bone sealant is very good.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A bone sealant composition suitable for staunching local hemorrhages on the bone, comprising: one or more polyester oligomers synthesized from glycerol, lactide, and glycolide; and one or more water-soluble polymers, which are polyethylene glycol, or copolymers of ethylene glycol and proplyene glycol, having a number average molecular weight of 6,000–10,000, or mixtures thereof.

2. A bone sealant composition according to claim 1, wherein said one or more polyester oligomers are synthesized from 1 part by mole of glycerol, X parts by mole of lactide and Y parts by mole of glycolide, where X and Y are, in each case independently of one another, 1, 2 or 3.

3. A bone sealant composition according to claim 2, wherein X+Y is ≦4.

4. A bone sealant composition according to claim 1, wherein the number average molecular weight of said one or more polyester oligomers is 200–1500.

5. A bone sealant composition according to claim 1, wherein the number average molecular weight of said one or more polyester oligomers is 300–1000.

6. A bone sealant composition according to claim 1, wherein said one or more polyester oligomers are synthesized from: 1 part by mole glycerol, 2 parts by mole lactide, and 1 part by mole glycolide; 1 part by mole glycerol, 2 parts by mole lactide, and 2 parts by mole glycolide; or 1 part by mole glycerol, 1 part by mole lactide, and 3 parts by mole glycolide.

7. A bone sealant composition according to claim 1, wherein the water-soluble polymer is polyethylene glycol and is 5–50% by weight of the composition.

8. A bone sealant composition according to claim 7, wherein the content of polyethylene glycol is 15–30% by weight of the composition.

9. A bone sealant composition according to claim 1, wherein the polyester oligomers are synthesized from 1 part by mole of glycerol, 1 part by mole of, D,L-lactide and 3 parts by mole of glycolide, the water-soluble polymer is polyethylene glycol, and the weight ratio of polyester oligomer to water soluble polymer is 70/30.

10. A method for staunching local hemorrhages on bone comprising applying a bone sealant composition according to claim 1 to the bone.

11. A method for applying active compounds to a bone comprising applying a bone sealant composition, as a carrier material, containing said active compounds to said bone, wherein said bone sealant composition is a composition according to claim 1.

12. A method for staunching local hemorrhages on bone comprising applying a bone sealant composition to the bone, wherein the bone sealant composition comprises one or more polyester oligomers synthesized from polyol, lactide, and glycolide; and one or more water-soluble polymers.

13. A bone sealant composition suitable for staunching local hemorrhages on the bone, comprising: one or more polyester oligomers synthesized from glycerol, lactide, and glycolide; and one or more water-soluble polymers, which are polyethylene glycol, or copolymers of ethylene glycol and propylene glycol, having a number average molecular weight of 6,000–10,000, or mixtures thereof, wherein said one or more polyester oligomers are synthesized from 1 part by mole of glycerol, X parts by mole of lactide and Y parts by mole of glycolide, where X and Y are, in each case independently of one another, 1, 2 or 3, and X+Y is ≦4.

14. A bone sealant composition suitable for staunching local hemorrhages on the bone, comprising: one or more polyester oligomers, synthesized from glycerol, lactide, and glycolide; and one or more water-soluble polymers, which are polyethylene glocol, or copolymers of ethylene glycol and propylene glycol, having a number average molecular weight of 6,000–10,000, or mixtures thereof, wherein said one or more polyester oligomers are synthesized from: 1 part by mole glycerol, 2 parts by mole lactide, and 1 part by mole glycolide; 1 part by mole glycerol, 2 parts by mole lactide, and 2 parts by mole glycolide; or 1 parts by mole glycerol, 1 part by mole lactide, and 3 parts by mole glyolide.

15. A bone sealant composition suitable for staunching local hemorrhages on the bone, comprising: one or more polyester oligomers synthesized from glycerol, lactide, and glycolide; and one or more water-soluble polymers, which are polyethylene glycol, or copolymers of ethylene glycol and propylene glycol, having a number average molecular weight of 6,000–10,000, or mixtures thereof, wherein the water-soluble polymer is polyethylene glycol and is 5–50% by weight of the composition.

16. A bone sealant composition according to claim 15, wherein the content of polyethylene glycol is 15–30% by weight of the composition.

17. A bone sealant composition suitable for staunching local hemorrhages on the bone, comprising: one or more polyester oligomers synthesized from glycerol, lactide, and glycolide; and one or more water-soluble polymers, which are polyethylene glycol, or copolymers of ethylene glycol and propylene glycol, having a number average molecular weight of 6,000–10,000, or mixtures thereof, wherein the polyester oligomers are synthesized from 1 part by mole of glycerol, 1 part by mole of D,L-lactide and 3 parts by mole of glycolide, the water-soluble polymer is polyethylene glycol, and the weight ratio of polyester oligomer to water soluble polymer is 70/30.

18. A method for staunching local hemorrhages on bone, comprising applying to the bone a bone sealant composition, comprising: one or more polyester oligomers synthesized from glycerol, lactide, and glycolide; and one or more water-soluble polymers, which are polyethylene glycol, or copolymers of ethylene glycol and propylene glycol, having a number average molecular weight of 6,000–10,000, or mixtures thereof.

19. A bone sealant composition according to claim 13, wherein the number average molecular weight of said one or more polyester oligomers is 200–1500.

20. A bone sealant composition according to claim 13, wherein the number average molecular weight of said one or more polyester oligomers is 300–1000.

21. A bone sealant composition according to claim 13, wherein said one or more water-soluble polymers are polyethylene glycol or copolyethers of ethylene glycol and propylene glycol.

* * * * *

UNITED STATES PATENT AND TRADEMARK OFFICE
CERTIFICATE OF CORRECTION

PATENT NO. : 6,420,454 B1
DATED : July 16, 2002
INVENTOR(S) : Wenz et al.

It is certified that error appears in the above-identified patent and that said Letters Patent is hereby corrected as shown below:

Column 6,
Line 43, reads "glocol." should read -- glycol. --

Signed and Sealed this

First Day of February, 2005

JON W. DUDAS
*Director of the United States Patent and Trademark Office*